United States Patent [19]

Asakura et al.

[11] Patent Number: 5,368,865
[45] Date of Patent: Nov. 29, 1994

[54] SUSPENDIBLE COMPOSITION AND PROCESS FOR PREPARING THE SAME

[75] Inventors: Sotoo Asakura, Kyoto; Yasuto Koyama, Itami; Youhei Kiyota, Ikeda; Kiyoko Akashi, Takarazuka; Akira Kagayama, Ikoma; Yoshio Murakami; Toshiomi Nakate, both of Kobe, all of Japan

[73] Assignee: Fujisawa Pharmaceutical Co., Ltd., Osaka, Japan

[21] Appl. No.: 97,617

[22] Filed: Jul. 27, 1993

Related U.S. Application Data

[63] Continuation of Ser. No. 788,041, Nov. 5, 1991, abandoned.

[30] Foreign Application Priority Data

Nov. 8, 1990 [JP] Japan ................... 2-304839
Mar. 7, 1991 [GB] United Kingdom .................. 9104834
Oct. 7, 1991 [JP] Japan ................... 3-259358

[51] Int. Cl.⁵ ............................ A61K 9/10; A61K 9/14
[52] U.S. Cl. .................... 424/489; 424/427; 514/912; 514/937; 514/975; 514/970; 514/885; 514/952
[58] Field of Search ............... 424/489, 427; 514/912, 514/937, 975

[56] References Cited

FOREIGN PATENT DOCUMENTS 184162 11/1986 European Pat. Off. .
61-148181 6/1986 Japan .

OTHER PUBLICATIONS

Transplantation, vol. 45, No. 1, pp. 206–209, Jan. 1988, N. Inamura, et al., "Prolongation of Skin Allograft Survival in Rats by a Novel Immunosuppressive Agent, FK506".
ACTA Societatis Ophthalmologicae Japonicae, p. 152, Feb. 20, 1988, (with partial English translation).

*Primary Examiner*—Thurman K. Page
*Assistant Examiner*—James M. Spear
*Attorney, Agent, or Firm*—Oblon, Spivak, McClelland, Maier, & Neustadt

[57] ABSTRACT

A suspendible composition comprising a tricyclic compound such as FK 506 substance which is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, or the like, and a pharmaceutically acceptable surfactant, which can be used as an orally administrable agent or eye drops and is useful for treating various diseases.

7 Claims, No Drawings

SUSPENDIBLE COMPOSITION AND PROCESS FOR PREPARING THE SAME

This application is a continuation of application Ser. No. 07/788,041, filed on Nov. 5, 1991, now abandoned.

BACKGROUND OF THE INVENTION

1. Field of the Invention

The present invention relates to a suspendible composition comprising fine particles of a tricyclic compound or its pharmaceutically acceptable salt and a pharmaceutically acceptable surfactant. The suspendible composition according to the present invention is useful as an orally administrable agent or eye drops.

2. Prior Art

Tricyclic compounds as shown by the below-mentioned general formula (I) and pharmaceutically acceptable salts thereof used in this invention have been known to possess excellent pharmacological activities such as immunosuppressive activity and antimicrobial activity, thereby useful for treating and/or preventing rejection against organs or tissue transplantation, graft versus host reaction, various autoimmune diseases and infectious diseases (Japanese Laid-Open Patent Application No. 61(1986)-148181, EP-A-0323042).

Particularly, FR 900506 substance which equals to FK 506 substance, FR 900520 substance, FR 900523 substance and FR 900525 substance are produced by fermenting Genus Streptomyces, in particular, *Streptomyces tsukubaensis* No. 9993 (FERM BP-927) or *Streptomyces hygroscopicus subsp. yakushimaensis* No. 7238 (FERM BP-928). Particularly, FK 506 substance represented by the following formula possesses excellent immunosuppressive activity, thus useful for treating and/or preventing rejection against organs transplantation and diseases in the ophthalmology. FK 506 substance:

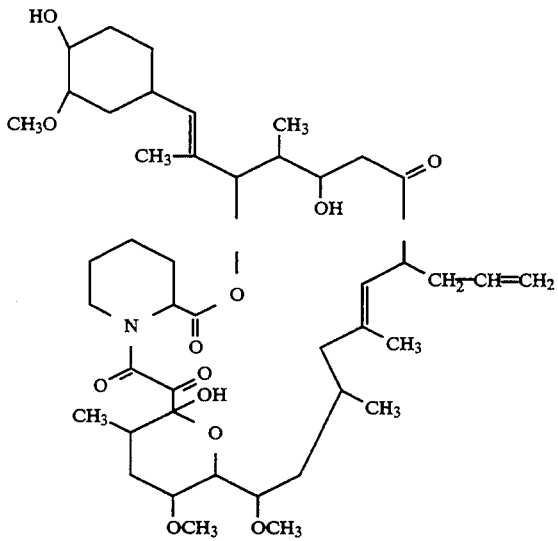

Chemical name: 17-allyl-1,14-dihydroxy-12-[2-(4-hydroxy-3-methoxycyclohexyl)-1-methylvinyl]-23,25-dimethoxy13,19,21,27-tetramethyl-11,28-dioxa-4-azatricyclo[22.3.1.0$^{4,9}$$^{1}$]octacos-18-ene-2,3,10,16-tetraone.

Injections or capsules for oral use of the tricyclic compound (I) have already been studied. The capsules are generally desirable preparation than the injections from the viewpoint of convenience, but would be difficult to slightly also is not so easy to use for children. Thus, there is a demand for the development of liquid formulations which are excellent in absorption ability when administered orally.

When the tricyclic compound (I) of the present invention is employed in ophthalmology, a concern is caused about the appearance of systemic adverse effect upon its oral administration, intramuscular injection or intravenous injection. Accordingly, eye drops for local administration are preferable in ophthalmology as a formulation capable of reducing the appearance of the adverse effect and attaining the desired object with less administration amount.

The tricyclic compound (I) of the present invention is well-soluble in organic solvents and fats and fatty oils, whereas it is very slightly soluble in water. Therefore, the tricyclic compound (I) is made into oily eye drops or ophthalmic ointments, similar to the general slightly soluble agents, to be used in ophthalmology. However, the oily eye drops or ophthalmic ointments of the compound (I) are disadvantageous in that the tricyclic compound (I) is remarkably poor in penetration into ocular tissues and additionally are accompanied with evanescent paropsia or unadjust pleasantness, thus unpractical.

Consequently, there has arisen a strong demand for the development of eye drops comprising the tricyclic compound (I) and having improvements in penetration into ocular tissues and in the aforesaid drawbacks.

SUMMARY OF THE INVENTION

The present invention provides a suspendible composition comprising fine particles of a tricyclic compound represented by the following formula (I):

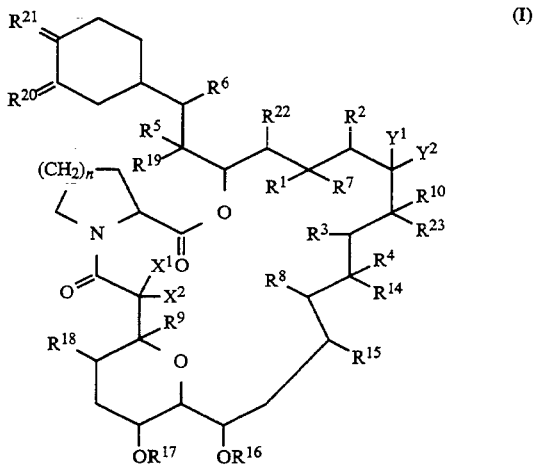

wherein each of adjacent pairs of $R^1$ and $R^2$, $R^3$ and $R^4$ or $R^5$ and $R^6$ independently (a) is two adjacent hydrogen atoms, or (b) may form another bond formed between the carbon atoms to which they are attached, and further, $R^2$ is an alkyl group;

$R^7$ is a hydrogen atom, a hydroxy group, a protected hydroxy group or an alkoxy group, or an oxo group together with $R^1$;

$R^8$ and $R^9$ each is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;

$X^1$ is a hydrogen atom or a hydroxy group;

$X^2$ is a hydrogen atom; or $X^1$ and $X^2$ may together represent an oxo group or —$CH_2O$—;

$Y^1$ is a hydrogen atom or a hydroxy group;

$Y^2$ is a hydrogen atom; or $Y^1$ and $Y^2$ may together represent an oxo group, N—$NR^{11}R^{12}$ or N—$OR^{13}$;

$R^{11}$ and $R^{12}$ each is independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ each is independently a hydrogen atom or an alkyl group;

$R^{20}$ and $R^{21}$ each is an oxo group or independently ($R^{20}$a and a hydrogen atom) or ($R^{21}$a and a hydrogen atom) in which $R^{20}$a and $R^{21}$a each independently is a hydroxy group, an alkoxy group or a group represented by the formula —$OCH_2OCH_2CH_2OCH_3$, or $R^{21}$a is a protected hydroxy group, or $R^{20}$a and $R^{21}$a may together represent an oxygen atom in an epoxide ring;

n is an integer of 1, 2 or 3;

in addition to their above definitions, four of $Y^1$, $Y^2$, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy, an alkoxy, benzyl and a group of the formula —$CH_2Se(C_6H_5)$;

or a pharmaceutically acceptable salt thereof, said fine particles of the tricyclic compound and its pharmaceutically acceptable salt having the average size of 5 μm or below; and a pharmaceutically acceptable surfactant, and optionally an aqueous medium.

The present invention also provides a process for preparing the above suspendible composition.

PREFERRED EMBODIMENTS OF THE INVENTION

Preferable examples and explanations for various definitions included in the scope of this invention will be detailed hereinbelow.

The term "suspendible composition" means a composition capable of suspending in an aqueous medium. The suspendible composition includes the one already suspended in an aqueous medium and the one which will be suspended therein on use.

The term "lower" as used in this specification means, unless otherwise indicated, a group having 1 to 6 carbon atoms.

Preferable examples of the "alkyl groups" are a straight or branched chain aliphatic hydrocarbon residue, for example, a lower alkyl group such as methyl, ethyl, propyl, isopropyl, butyl, isobutyl, pentyl, neopentyl, hexyl and the like.

Preferable examples of the "alkenyl groups" are a straight or branched chain aliphatic hydrocarbon residue having one double-bond, for example, a lower alkenyl group such as vinyl, propenyl, butenyl, methylpropenyl, pentenyl, hexenyl and the like.

Examples of the "aryl groups" include phenyl, tolyl, xylyl, cumenyl, mesityl, naphthyl and the like.

Preferable protective groups in the "protected hydroxy groups" are 1-(lower alkylthio)(lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_{1-4}$ alkylthiomethyl group, most preferably methylthiomethyl group; trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenylsilyl, etc.), more preferably tri($C_{1-4}$)alkylsilyl group and $C_{1-4}$ alkyldiphenylsilyl group, most preferably tertbutyldimethylsilyl group and tert-butyldiphenylsilyl group; or an acyl group such as an aliphatic or aromatic acyl group derived from a carboxylic acid, sulfonic acid and carbamic acid, or an aliphatic acyl group substituted by an aromatic group.

Examples of the aliphatic acyl groups are a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group or a lower alkylcarbamoyl group having one or more substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl group such as tri(lower)alkylsilyl(lower)alkoxycarbonyl(lower)alkylcabamoyl group (e.g., trimethylsilylmethoxycarbonylethylcarbamoyl, trimethylsilylethoxycarbonylpropylcarbamoyl, triethylsilylethoxycarbonylpropylcarbamoyl, tertiary butyldimethylsilylethoxycarbonylpropylcarbamoyl, trimethylsilylpropoxycarbonylbutylcarbamoyl, etc.) and so on.

Examples of the aromatic acyl groups are an aroyl group optionally having one or more suitable substituents such as nitro, e.g., benzoyl, toluoyl, xyloyl, naphthoyl, nitrobenzoyl, dinitrobenzoyl, nitronaphthoyl etc.; or an arenesulionyl group optionally having suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by aromatic group include ar(lower)alkanoyl group optionally having one or more substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_{1-4}$ alkanoyl group optionally having carboxy, cyclo($C_{5-6}$)alkoxy($C_{1-4}$)alkanoyl group having two ($C_{1-4}$)alkyl at the cycloalkyl moiety, camphorsulfonyl group, carboxy($C_{1-4}$)alkylcarbamoyl group, tri($C_{1-4}$)alkylsilyl($C_{1-4}$)alkoxycarbonyl($C_{1-4}$)alkylcarbamoyl group, benzoyl group optionally having one or two nitro groups, benzenesulfonyl group having halogen or phenyl($C_{1-4}$)alkanoyl group having $C_{1-4}$alkoxy and trihalo($C_{1-4}$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Examples of the "heterocyclic groups" in the saturated or unsaturated 5- or 6-membered nitrogen, sulfur and/or oxygen containing ring include a pyrrolyl group or a tetrahydrofuryl group.

The pharmaceutically acceptable salts of the compounds (I) include conventional non-toxic and pharmaceutically acceptable salts such as the salts with inorganic or organic bases, specifically, an alkaline metal salt such as sodium salt or potassium salt, an alkaline earth metal salt such as calcium salt or magnesium salt, an ammonium salt or an amine salt such as triethylamine salt or N-benzyl-N-methylamine salt.

With respect to the tricyclic compound (I) of this invention, it is to be understood that there may be one or more conformers or stereoisomers such as optical and geometrical isomers due to asymmetric carbon atom(s) and double bond(s), and such isomers are also included within a scope of this invention.

According to the present invention, the tricyclic compound (I) or its salt is required to be used as fine particles having the average size of 5 μm or below. The particles may be either of crystalline or amorphous ones. The fine particles preferably have an average size of 3 μm or below, or 2 μm or below, for example, 0.9 μm, 0.8 μm or 0.7 μm. Such average size is significantly very small compared to the particle size of 75 μm or below which is preferable to use suspension type of eye drops (refer to the explanation of eye drops in Japanese Pharmacopoeia) or general particle size of 10 μm or below.

The fine particles of the tricyclic compound (I) or its pharmaceutically acceptable salt used in the present invention can be prepared by the following process.

It comprises a step of dissolving the tricyclic compound (I) (including its salt hereinbelow) in a solvent and a step of precipitation from the solution obtained by the previous step. Examples of the solvents used for dissolving the compound (I) include organic solvents capable of dissolving the compound (I), especially organic solvents having a large solubility toward the compound (I) and compatibility with water, for example, alcohols such as ethanol, acetone, acetonitrile, dioxane or the like. The amount of the solvent to be used is preferably 3 to 10 times that of the compound (I). A surfactant, such as nonionic surfactant should be added to the solution. The surfactant may be added to the solvent before dissolving the compound (I) therein. Otherwise, an aqueous surfactant solution may be prepared in advance.

Subsequently, water is added to the obtained solution which is then vigorously stirred to precipitate crystals. The mixture including the crystals is subjected to aging, concentration and micronization (e.g., ultrasonification) if necessary. The mixture mentioned above is finally passed through a filter having a predetermined mesh (e.g., millipore filter of 0.45 μm) to obtain a fine particle (which generally comprises fine crystals) having a desired particle size. Alternatively, the mixture is lyophilized after the micronization, thereby obtaining a lyophilized product of fine particles having a desired particle size. The lyophilized product includes the surfactant as well.

The preparation of the above-mentioned fine particles or lyophilized product may be performed after the addition of an anticoagulating agent, antifoaming agent, isotonic agent, buffer agent, preservatives, thickener or the like in a suitable amount.

Preferable pharmaceutically acceptable surfactants used for this invention are nonionic surfactants. Examples of the nonionic surfactant are as follows.

A. Ether type
  Polyoxyethylene alkyl ethers
  Polyoxyethylene polyoxypropylene block polymer
  Polyoxyethylene polyoxypropylene alkyl ethers
B. Ether-ester type
  Polyoxyethylene glycerine fatty acid esters
  Polyoxyethylene sorbitan fatty acid esters such as
  Polysorbate 80 (monooleic polyoxyethylene sorbitan)
  Polyoxyethylene sorbitol fatty acid esters
C. Ester type
  Polyethylene glycol fatty acid esters
  Polyglycerine fatty acid esters Preferably, the nonionic surfactant is HLB 9 or more and non-toxic to human body. More preferable one is polyoxyethylene sorbitan fatty acid esters.

The surfactant and the compound (I) in the suspendible composition of the present invention is preferably in the ratio of 0.01:1 to 5:1 by weight, more preferably 0.1:1 to 1:1 by weight.

The concentration of the tricyclic compound (I) in the suspendible composition of the present invention is not specifically limited, but is preferably 0.001 to 2 wt. %, more preferably 0.01 to 1 wt. % in the suspension to which an aqueous medium is added. The concentration of the surfactant varies with type, but generally 0.001 to 1 wt. %, more preferably 0.005 to 0.2 wt. % in the suspension to which the aqueous medium added.

If desired, the suspendible composition of the present invention may contain conventional additives which are used in solutions or eye drops, such as anticoagulating agents (e.g., hydroxypropylmethylcellulose, D-mannitol or the like); anti-foaming agents (e.g., silicons such as simethicone); isotonic agents (e.g., sodium chloride or the like); buffer agents (e.g., boric acid, sodium hydrogen phosphate, sodium dihydrogen phosphate, or the like); preservatives (e.g., benzalkonium chloride, benzethonium chloride, chlorobutanol, methylparaben, propylparaben or the like); thickening agents (e.g., saccharides such as lactose, mannitol, maltose or the like, hyaluronic acid or its salt such as sodium hyaluronate, potassium hyaluronate or the like, mucopolysaccharides such as chondroitin sulfate or the like, sodium polyacrylate, carboxyvinylpolymer, cross-linked polyacrylate or the like) and other additives.

The suspendible composition of the present invention can be prepared by adding, to the fine particle (average particle size: 5 μm or below) of the tricyclic compound (I) or its salt or the lyophilized product obtained as mentioned above, the surfactant or its aqueous solution (the latter is used if required when the tricyclic compound (I) is in the form of lyophilized product), and optionally additives such as anticoagulating agent, antifoaming agent, isotonic agent, buffer agent, preservative and/or thicking agent in a suitable amount, the resultant being then well mixed.

Preferably, the tricyclic compound (I) or its salt is in the form of a composition which can be used as an aqueous suspension by addition of an aqueous medium in situ from the viewpoint of stability of the tricyclic compound (I).

The therapeutically effective dose of the tricyclic compound (I) or its salt varies with age and kinds or level of diseases of each patient, but generally 0.01 to 1000 mg per day, preferably 0.1 to 500 mg per day, and more preferably 0.5 to 100 mg per day. Usually, the tricyclic compound (I) or its salt is administered in an average amount of 0.5 mg, 1 mg, 5 mg, 10 mg, 50 mg, 100 mg, 250 mg, and 500 mg per day.

The eye drops including the tricyclic compound (I) or its salt is usually applied to an eye in 2 to 3 drops, one to several times per day.

The suspendible composition of the present invention can also be prepared by employing the compounds disclosed in the following publications such as EP-A-353678, Japanese Patent Application No. HEI 2(1990)-74330, PCT/GB90/01262, EP-A-413532, PCT/JP91/00314, British Patent Application No. 9012963.6, British Patent Application No. 9014136.7, British Patent Application No. 9014681.2, British Patent Application No. 9014880.0, British Patent Application No. 9014881.8, British Patent Application No. 9015098.8, British Patent Application No. 9016115.9, British Patent Application No. 9016693.5, EP-A-323865, EP-A-349061, EP-A-358508, EP-A364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576 A, EP-A-402931 and EP-A-427680.

The present invention will be explained hereinbelow with reference to the Examples.

EXAMPLE 1

Preparation of Fine Particles of FK 506 Substance

FK 506 substance (3 g) was dissolved in ethanol (15 ml), to which 10% aqueous hardened polyoxyethylene castor oil solution (HCO-60 ®: manufactured by Nikko Chemicals Co. Ltd.) or 10% aqueous monooleic polyoxyethylene sorbitan 20EO solution (polysorbate 80, Reodol TWO-120 ®: manufactured by Kao-Atras Co., Ltd.) (6 ml each) was added dropwise under stirring. Thereafter, distilled water (9 ml) was dropwise added in a small amount under slow stirring at 25° C. Further, distilled water (80 ml) was added under rapid stirring and further stirred for about 15 minutes. Finally, distilled water (60 ml) was added under rapid stirring to precipitate crystals of FK 506 substance which was allowed to stand overnight at 25° C. The suspension thus obtained was subjected to ultrasonic wave treatment for 2 minutes to disperse and filtered through a filter (Millipore Co., Ltd.) having a pore size of 0.45 µm under reduced pressure to obtain wet crystals (average particle size: 0.9 µm) of FK 506 substance.

Fine particles of various particle sizes were prepared by the same manner as described above.

Subsequently, prescription examples of the present invention will be explained.

Prescription 1

| | |
|---|---|
| FK 506 substance (average particle size:0.8 µm) | 1.0% |
| Polyoxyl stearate 40 (dispersing agent) | 0.05% |
| Benzalkonium chloride (preservative) | 0.02% |
| Sodium chloride (isotonic agent) | 0.288% |
| Phosphate buffer (pH 4.5) q.s. | to 100 |

Each component was mixed according to a known method to afford aqueous suspendible eye drops.

Aqueous suspensions for eye drops of the Prescription 2 to Prescription 6 were prepared by the same manner as in Prescription 1.

Prescription 2

| | |
|---|---|
| FK 506 substance (average particle size:3.0 µm) | 0.5% |
| Polysorbate 80 (dispersing agent) | 0.05% |
| Polyvinyl alcohol (dispersing agent) | 0.28% |
| Chlorobutanol (preservatives) | 0.5% |
| Glycerine (isotonic agent) | 2.47% |
| Phosphate buffer (pH 4.5) q.s. | to 100 |

Prescription 3

| | |
|---|---|
| FK 506 substance (average particle size:2.0 µm) | 0.2% |
| Polyoxyethylene polyoxypropylene ethyl ether (dispersing agent) | 0.1% |
| Polyvinylpyrrolidone (dispersing agent) | 0.06% |
| Methylparaben (preservatives) | 0.04% |
| Propylparaben (preservatives) | 0.02% |
| Glycerine (isotonic agent) | 2.47% |
| Phosphate buffer (pH 5.0) q.s. | to 100 |

Prescription 4

| | |
|---|---|
| FK 506 substance (average particle size:1.5 µm) | 0.1% |
| Polysorbate 80 | 0.05% |
| Polyvinylalcohol | 0.28% |
| Benzalkonium chloride | 0.02% |
| Sodium chloride | 0.280% |
| Phosphate buffer (pH 4.5) q.s. | to 100 |

Prescription 5

| | |
|---|---|
| FK 506 substance (average particle size:0.9 µm) | 0.1% |
| Polysorbate 80 | 0.05% |
| Benzalkonium chloride | 0.02% |
| Phosphate buffer (pH 4.5) q.s. | to 100 |

Prescription 6

| | |
|---|---|
| FK 506 substance (average particle size:0.9 µm) | 0.1% |
| Polysorbate 80 | 0.05% |
| Benzalkonium chloride | 0.02% |
| Sodium chloride | 0.288% |
| Phosphate buffer (pH 4.5) q.s. | to 100 |

Prescription 7

| | |
|---|---|
| FK 506 substance (average particle size:1.0 µm) | 1.0 mg |
| Polysorbate 80 | 1.0 mg |
| Polyvinylalcohol | 2.8 mg |
| Methylparaben | 0.8 mg |
| Propylparaben | 0.2 mg |
| Citric acid | 5.0 mg |
| Sodium hydroxide: suitable amount for adjusting pH 4.5 | |
| Purified water q.s. | to 1.0 ml |

Each component was mixed by a conventional method to prepare an oral aqueous suspension.

Prescription 8

| | |
|---|---|
| Suspendible Composition | |
| FK 506 substance (average particle size:1.0 µm) | 50 mg |

| -continued | |
|---|---|
| Polysorbate 80 | 25 mg |
| Hydroxypropylmethylcellulose (TC-5S) | 150 mg |
| Simethicone (i.e., dimethyl polysiloxance, silicon anti-foaming agent) | 2 mg |
| D-Mannitol | 250 mg |
| Dispersing Medium | |
| Methylparaben | 40 mg |
| Propylparaben | 10 mg |
| Purified water q.s. | to 50 ml |

A solution of polysorbate 80 in purified water was added to a solution of FK 506 substance in ethanol followed by well mixing. To the resultant was gradually added an appropriate amount of water to crystallize out FK 506 substance. The resultant mixture was aged, concentrated and subjected to ultrasonic wave treatment. The mixture was mixed and suspended in a solution of hydroxypropylmethylcellulose and D-mannitol in purified water. The resultant was poured into a vessel filled with simethicone and then lyophilized to afford the suspendible composition.

On the other hand, methylparaben and propylparaben were dissolved in purified water to afford the dispersing medium. An aqueous suspension can be prepared by adding the aforesaid dispersing medium to the aforesaid suspendible composition, if required.

The effect of the present invention will be explained hereinbelow with reference to Test Examples.

1. Absorption Test by Applying Eye Drops
Eye drop to be tested
Eye drop (1) . . . obtained in Prescription 5
Test method The test eye drop was applied five times to both eyes of 8–10-week old male SD-rats (weight: 275 to 405 g) in an amount of 10 μl at an interval of 5 minutes. After an hour, the rats were bled to death for extracting both eyes. The concentration of FK 506 substance at the cornea and retina and choroid of the extracted eyes was measured in accordance with a known enzyme immunoassay (e.g., indirect method disclosed in Japanese Laid-Open Patent Publication No. HEI 1-92659).

The results were shown in Tables 1 and 2. The concentration was represented by mean ± standard error of mean.
Results

TABLE 1

| (concentration of FK 506 substance at cornea) | |
|---|---|
| Eye Drop | Conc. of FK 506 substance [ng/tissue wt. (g)] After an hour |
| Eye Drop (1) | 374.3 ± 110.9 |

TABLE 2

| (conc. of FK 506 substance at retina and choroid) | |
|---|---|
| Eye Drop | Conc. of FK 506 substance [ng/tissue wt. (g)] After an hour |
| Eye Drop (1) | 22.5 ± 1.7 |

2. Absorption Test by Oral Administration
Oral Agent to Be Tested
The aqueous suspension obtained in Prescription 7 was used.
Test Method
The oral agent mentioned above was diluted with purified water to have the concentration of FK 506 substance of 0.064 mg/ml. The resultant was orally administered to six cynomolgus monkeys (0.32 mg/kg).

The concentration of FK 506 substance in whole blood was measured 0.5, 1, 2, 4 and 6 hours after the administration in accordance with the aforesaid enzyme immunoassay.

The results are shown in Table 3. The test results are represented by the average ± standard error.

TABLE 3

| (conc. of FK 506 substance in whole blood) | |
|---|---|
| Time | Conc. in whole blood (ng/ml) |
| 0.5 | 13.38 ± 9.88 |
| 1 | 18.65 ± 9.36 |
| 2 | 18.63 ± 9.89 |
| 4 | 15.33 ± 7.77 |
| 6 | 12.45 ± 9.33 |

As apparent from the above, the suspendible composition of the present invention can provide a formulation having excellent penetration into internal tissues, especially a formulation exhibiting excellent penetration into internal tissues through oral administration and ocular tissues through application to an eye.

Accordingly, the present invention can provide a formulation of the tricyclic compound (I) which is easy to adjust the administration amount, is excellent in stability, dispersibility and penetration into ocular tissues, is capable of applying to eye and is easy to administer to children. The formulation of the present invention can also aspirate.

In view of pharmacological activities of the tricyclic compound (I) such as immunosuppressive activity, antimicrobial activity, and the like, the formulation of the present invention is useful for the treatment and prevention of immune-mediated diseases such as the resistance by transplantation of organs or tissue such as heart, kidney, liver, medulla ossium, skin, cornea, lung, pancreas, intestinum tenue, limb, muscle, nervus, etc.; graft-versus-host diseases by medulla ossium transplantation; autoimmune diseases such as rheumatoid arthritis, systemic lupus erythematosus, Hashimoto's thyroiditis, multiple sclerosis, myasthenia gravis, type I diabetes, and the like; and further infectious diseases caused by pathogenic microorganisms.

Further, the formulation of the present invention is useful for the treatment and the prophylaxis of inflammatory and hyperproliferative skin diseases and cutaneous manifestations of immunologically-mediated illnesses, such as, psoriasis, atopical dermatitis, contact dermatitis and further eczematous dermatitises, seborrhoeis dermatitis, Lichen planus, Pemphigus, bullous Pemphigoid, Epidermolysis bullosa, urticaria, angioedemas, vasculitides, erythemas, cutaneous eosinophilias, Lupus erythematosus, acne and Alopecia areata;

various eye diseases such as autoimmune diseases and so on (e.g. keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' ophthalmopathy, Vogt-Koyanagi-Harada syndrome, sarcoidosis, etc.);

reversible obstructive airways disease, which includes conditions such as asthma (e.g., bronchial asthma, allergic asthma, intrinsic asthma, extrinsic asthma and dust asthma), particularly chronic or inveterate asthma (e.g., late asthma and airway hyperresponsiveness), bronchitis and the like;

inflammation of mucosa and blood vessels such as gastric ulcers, vascular damage caused by ischemic diseases and thrombosis, ischemic bowel disease, inflammatory bowel disease, necrotizing enterocolitis, intestinal lesions associated with thermal burns, leukotriene B$_4$-mediated diseases;

intestinal inflammations/allergies such as Coeliac disease, proctitis, eosnophilic gastroenteritis, mastocytosis, Crohn's disease and ulcerative colitis;

food related allergic diseases which have symptomatic manifestation remote from the gastro-intestinal tract, for example, migraine, rhinitis and eczema;

renal diseases such as interstitial nephritis, Goodpasture's syndrome, hemolytic-uremic syndrome and diabetic nephropathy;

nervous diseases such as multiple myositis, Guillain-Barré syndrome, Ménière's disease and radiculopathy;

endocrine diseases such as hyperthyroidism and Basedow's disease;

hematic diseases such as pure red cell aplasia, aplastic anemia, hypoplastic anemia, idiopathic thrombocytopenic purpura, autoimmune hemolytic anemia, agranulocytosis and anerythroplasia;

bone diseases such as osteoporosis;

respiratory diseases such as sarcoidosis, fibroid lung and idiopathic interstitial pneumonia;

skin diseases such as dermatomyositis, leukoderma vulgaris, ichthyosis vulgaris, photoallergic sensitivity and cutaneous T cell lymphoma;

circulatory diseases such as arteriosclerosis, atherosclerosis, aortitis syndrome, polyarteritis nodosa and myocardosis;

collagen diseases such as scleroderma, Wegener's granuloma and Sjogren's syndrome;

adiposis;

eosinophilic fasciitis;

periodontal disease such as lesion of gingiva, periodontium, alveolar bone, substantia ossea dentis;

nephrotic syndrome such as glomerulonephritis;

male pattern alopecia or alopecia senilis;

muscular dystrophy;

Pyoderma and Sezary's syndrome;

active oxgen-mediated diseases, for example, organ injury such as ischemia-reperfusion injury of organs (e.g., heart, liver, kidney, digestive tract) which occurs on preservation, transplantation or ischemic diseases (e.g., thrombosis, cardiac infarction): intestinal diseases such as endotoxin-shock, pseudomembranous colitis, colitis caused by drug or radiation: renal diseases such as ischemic acute renal insufficiency, chronic renal insufficiency: pulmonary diseases such as toxinosis caused by lung-oxygen or drug (e.g., paracort, bleomycins), lung cancer, pulmonary emphysema: ocular diseases such as cataracta, siderosis, retinitis, pigmentosa, senile macular degeneration, vitreal scarring, corneal alkali burn: dermatitis such as erythema multiforme, linear IgA ballous dermatitis, cement dermatitis: and others such as gingvatis, periodontitis, sepsis, pancreatitis, diseases caused by environmental pollution (e.g., air pollution), aging, carcinogenis, metastasis of carcinoma, hypobaropathy; diseases caused by histamine or leukotriene C$_4$ release; and so on.

Further, the active ingredient of the present invention has liver regenerating activity and/or activities of stimulating hypertrophy and hyperplasia of hepatocytes. Therefore, the formulation of the present invention is useful for the treatment and prevention of hepatic diseases such as immunogenic diseases (e.g., chronic autoimmune liver diseases such as the group consisting of autoimmune hepatitis, primary biliary cirrhosis and sclerosing cholangitis), partial liver resection, acute liver necrosis (e.g., necrosis caused by toxins, viral hepatitis, shock or anoxia), B-virus hepatitis, non-A/non-B hepatitis, cirrhosis and hepatic failure such as fulminant hepatic failure, late-onset hepatic failure and "acute-on-chronic" liver failure (acute liver failure on chronic liver diseases).

Moreover, the formulation of the present invention is useful for various diseases because of its useful pharmaceutical activity such as augmenting activity of chemotherapeutic effect, preventing or treating activity of cytomegalovirus infection, anti-inflammatory activity, and so on.

What is claimed is:

1. A composition suspendable in an aqueous medium comprising fine particles of a tricyclic compound represented by the following formula (I):

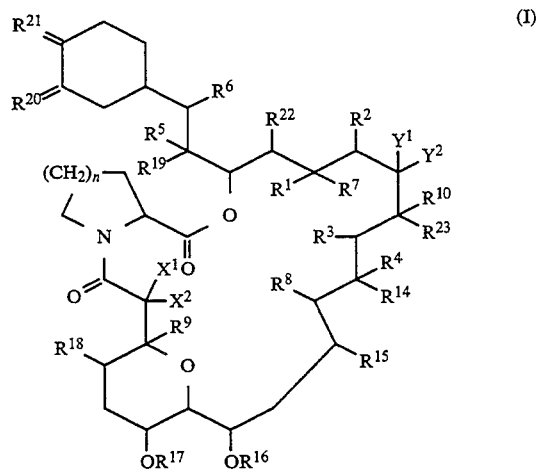

wherein each of adjacent pairs of $R^1$ and $R^2$, $R^3$ and $R^4$ or $R^5$ and $R^6$ independently
   (a) is two adjacent hydrogen atoms, or
   (b) may form another bond formed between the carbon atoms to which they are attached, $X^1$ is a hydrogen atom or a hydroxy group;

$X^2$ is a hydrogen atom; or $X^1$ and $X^2$ may together represent an oxo group or —CH$_2$O—;

$Y^1$ is a hydrogen atom or a hydroxy group;

$Y^2$ is a hydrogen atom; or $Y^1$ and $Y^2$ may together represent an oxo group, N—NR$^{11}$R$^{12}$ or N—OR$^{13}$;

$R^{11}$ and $R^{12}$ each is independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ each is independently a hydrogen atom or an alkyl group;

$R^{20}$ and $R^{21}$ each is an oxo group or independently ($R^{20}$a and a hydrogen atom) or ($R^{21}$a and a hydrogen atom) in which $R^{20}$a and $R^{21}$a each is independently a hydroxy group, an alkoxy group or a group represented by the formula 'OCH$_2$OCH$_2$CH$_2$OCH$_3$, or $R^{21}$a is a protected hydroxy group, or $R^{20}$a and $R^{21}$a may together represent an oxygen atom in an epoxide ring;

n is an integer of 1, 2 or 3; and in addition to their above definitions, four of $Y^1$, $Y^2$, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy, an alkoxy, benzyl and a group of the formula —CH$_2$Se(C$_6$H$_5$);

or a pharmaceutically acceptable salt thereof, said fine particles of the tricyclic compound or its pharmaceutically acceptable salt having an average size of 5 μm or below; and a pharmaceutically acceptable nonionic surfactant selected from the group consisting of polyoxyethylene sorbitan fatty acid esters, polyoxyethylene polyoxypropropylene alkyl ethers and polyethylene glycol fatty acid esters, the HLB of which is 9 and more; and in which the nonionic surfactant and the tricyclo compound is in the ratio of 0.01:1 to 5:1 by weight.

2. The composition as claimed in claim 1, in which the nonionic surfactant is polysorbate 80.

3. The composition as claimed in claim 1, in which the tricyclic compound (I) is one wherein each of adjacent pairs of $R^3$ and $R^4$ or $R^5$ and $R^6$ independently may form another bond formed between the carbon atoms to which they are attached, $R^8$ and $R^{23}$ each is independently a hydrogen atom;

$R^9$ is a hydroxy group;

$R^{10}$ is methyl, ethyl, propyl or allyl;

$X^1$ is a hydrogen atom;

$X^2$ is a hydrogen atom; or $X^1$ and $X^2$ may together represent an oxo group;

$Y^1$ and $Y^2$ may together represent an oxo group;

$R^{14}$, $R^{15}$, $R^{16}$, $R^{17}$, $R^{18}$, $R^{19}$ and $R^{22}$ each is independently methyl;

$R^{20}$ and $R^{21}$ independently are ($R^{20}$a and a hydrogen atom) or ($R^{21}$a and a hydrogen atom) in which $R^{20}$a and $R^{21}$a each is a hydroxy group or an alkoxy group or $R^{21}$a is a protected hydroxy group; and n is an integer of 1 or 2.

4. The composition as claimed in claim 1, in which the tricyclic compound (I) is one wherein $R^7$ is a hydrogen atom, a hydroxy group or a protected hydroxy group;

$X^1$ and $X^2$ may together represent an oxo group;

$R^{20}$a is methoxy; and $R^{21}$a is a hydroxy or protected hydroxy group.

5. The composition as claimed in claim 4 in which the tricyclic compound (I) is 17-allyl-1,14-dihydroxy-12-[2-(4-hydroxy-3-methoxycyclo-hexyl),1-methylvinyl]-23,25-dimethoxy13,19,21,27-tetramethyl-11,28-dioxa-4-azatricyclo[22.3.10$^4$,9]-octacos-18-ene-2,3,10,16-tetraone or 17-ethyl-1,14-dihydroxy-12-[2-(4-hydroxy-3-methoxycyclohexyl)1-methylvinyl]-23,25-dimethoxy-13,19,21,27-tetramethyl-11,28-dioxa-4-azatricyclo[22.3.10$^{4,9}$]octacos-18-ene-2,3,10,16-tetraone.

6. An aqueous suspension comprising the composition of claim 1.

7. The aqueous suspension as claimed in claim 6 which is in the form of aqueous eye drops.

* * * * *

UNITED STATES PATENT AND TRADEMARK OFFICE
CERTIFICATE OF CORRECTION

PATENT NO. : 5,368,865　　　　　　　　　　Page 1 of 3

DATED : NOVEMBER 29, 1994

INVENTOR(S) : SOTOO ASAKURA ET AL.

It is certified that error appears in the above-identified patent and that said Letters Patent is hereby corrected as shown below:

Column 1: line 63, "dimethoxy13,19,21,27-"
　should read　　--dimethyoxy-13,19,21,27- --;

line 64, "$1.0^{4,91}$"
　should read　　--$1.0^{4,9}$--.

Column 2: line 1,　"cult to slightly also is not so easy to use for children"
　should read　　--cult to slightly adjust an administration amount of active ingredient and also is not so easy to use for children--.

line 25,　"cent paropsia or unadjust pleasantness, thus unpractical"
　should read　　--cent paropsia or unpleasantness, thus unpractical--

Column 4: line 38,　"alkylcabamoyl"
　should read　　--alkylcarbamoyl-- line 51, "chlorobenzenesulfonyl"
　should read:　--chlorobenzenesulfonyl--

UNITED STATES PATENT AND TRADEMARK OFFICE
CERTIFICATE OF CORRECTION

PATENT NO. : 5,368,865

DATED : NOVEMBER 29, 1994

INVENTOR(S) : SOTOO ASAKURA ET AL.

It is certified that error appears in the above-identified patent and that said Letters Patent is hereby corrected as shown below:

Column 12: between lines 44 and 45 insert,
--and further, $R^2$ is an alkyl group; $R^7$ is a hydrogen atom, a hydroxy group, a protected hydroxy group or an alkoxy group, or an oxo group together with $R^1$;
$R^8$ and $R^9$ each is independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;-- line 61, "formula 'OCH$_2$OCH$_2$CH$_2$OCH$_3$"
should read: --formula -OCH$_2$OCH$_2$CH$_2$OCH$_3$--

Column 13, line 15: "polyoxypropylene"
should read: --polyoxypropylene--

UNITED STATES PATENT AND TRADEMARK OFFICE
CERTIFICATE OF CORRECTION

PATENT NO. : 5,368,865

DATED : NOVEMBER 29, 1994

INVENTOR(S) : SOTOO ASAKURA ET AL.

It is certified that error appears in the above-identified patent and that said Letters Patent is hereby corrected as shown below:

line 20:    "2-(4-hydroxy-3-methoxycyclo-hexyl),1-methylvinyl]-"
should read: --2-(4-hydroxy-3-methoxycyclohexyl)-1-methylvinyl]- -- line 21:    "dimethoxy13,19,21,27-"
should read: --dimethoxy-13,19,21,27- -- line 22:    "$10^{4,9}$"
should read: --$1.0^{4,9}$-- line 24:    "methoxycyclohexyl)1-methylvinyl]-"
should read: --methoxycyclohexyl)-1-methylvinyl]- -- line 26:    "$10^{4,9}$"
should read: --$1.0^{4,9}$--

Signed and Sealed this

Fourth Day of July, 1995

Attest:

BRUCE LEHMAN

Attesting Officer        Commissioner of Patents and Trademarks